(12) United States Patent
Rosenfeld et al.

(10) Patent No.: US 6,394,990 B1
(45) Date of Patent: May 28, 2002

(54) ADHESIVE PATTERNS FOR FEMININE HYGIENE ARTICLES

(75) Inventors: Leonard Geller Rosenfeld, East Windsor; Pramod Shantaram Mavinkurve, Princeton, both of NJ (US); Henri Brisebois, Lachenaie; Roger Boulanger, Ste-Julie Vercheres, both of (CA)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 09/702,032

(22) Filed: Oct. 30, 2000

Related U.S. Application Data

(62) Division of application No. 09/104,122, filed on Jun. 24, 1998, now Pat. No. 6,176,850.

(51) Int. Cl.[7] ................................................ A61F 13/15
(52) U.S. Cl. .................... 604/389; 604/386; 604/387
(58) Field of Search ..................... 604/385.03, 385.04, 604/387, 389, 390

(56) References Cited

U.S. PATENT DOCUMENTS 5,217,448 A * 6/1993 Glaug ........................ 604/397
5,429,630 A * 7/1995 Beal ......................... 604/385.1
5,478,336 A * 12/1995 Pigneul .................... 604/385.1

* cited by examiner

*Primary Examiner*—John G. Weiss
*Assistant Examiner*—C. Lynne Anderson
(74) *Attorney, Agent, or Firm*—James P. Barr

(57) ABSTRACT

A feminine hygiene article and method of making same so that back-attached wings have adhesive areas for attachment to an undergarment, that are substantially offset from the adhesive areas of the main body portion, also used to attach the undergarment.

7 Claims, 5 Drawing Sheets

ADHESIVE PATTERNS FOR FEMININE HYGIENE ARTICLES

This application is a divisional of application Ser. No. 09/104,122 filed Jun. 24, 1998 now U.S. Pat. No. 6,176,850.

FIELD OF THE INVENTION

This invention relates to a disposable feminine hygiene article having back-attached wings with adhesive to help secure the article to an undergarment, along with the adhesive areas on the main body portion of the article.

BACKGROUND OF THE INVENTION

Disposable feminine hygiene articles, which are understood here in to include sanitary napkins, pantiliners, and incontinence pads, feature a main body portion comprising an absorbent material mounted on an impervious backing sheet, the main body portion being bounded by a peripheral edge. (As used herein, "peripheral edge" refers to the extreme outside edge of the main body, however that edge happens to have been formed.) Frequently, such articles further include attachment wings or flaps contiguously extending from said backing sheet from opposite sides thereof. Because portions of both the backing sheet and the wings support adhesive areas, when the article is placed with the backing sheet in contact with one side of the crotch area of an undergarment, and the wings are wrapped around the other side of the crotch area, the two opposing adhesive areas hold the article in proper location on both sides of the undergarment.

Such wings are either contiguous extensions of the backing sheet, in which case they hinge and fold primarily about said peripheral edge of the main body portion, or, they are hingedly attached to the backing sheet along a fold line located inside the peripheral edge of the main body portion, hereinafter, "back-attached". A preferred manner of constructing the latter is to form the wings as a contiguous extension of the backing sheet, and then to fold them about the peripheral edge and adhesively secure a portion of the wing to a portion of the backing sheet inside the peripheral edge. This is preferred because it biases the wings to fold back towards the main body portion, exactly as the user does when wrapping the wings about an interposed undergarment. It has been found that such a bias renders easier the wrapping of the wings about the undergarment. Indeed, in the absence of the bias so provided, the wings may have a tendency to unfold and pull their adhesive areas off the undergarment.

Nevertheless, the helpful bias noted above has its own disadvantage. The adhesive areas on both the backing sheet and the wings are temporarily covered by release paper until the user is ready to install the article. However, once the release paper is removed, if the adhesive area of a wing inadvertently contacts directly the adhesive area of the backing sheet, the two stick together so well (in the absence of the intended undergarment), that they cannot be pulled apart without damaging the article. The noted bias of the wings towards the backing sheet has the disadvantage of making such inadvertent contact more, rather than less, likely.

Thus, there has been a need prior to this invention to prevent wing adhesive areas from sticking to the adhesive areas of the backing sheet, particularly when the wings are made by folding them about the peripheral edge and adhesively secured to the backing sheet to create the bias.

SUMMARY OF THE INVENTION

We have designed a disposable feminine hygiene article that solves the above-noted problems.

More specifically, in accord with one aspect of the invention, there is provided a disposable feminine hygiene article comprising:
  a main body portion comprising an absorbent material and an impervious backing sheet on which the material is mounted, the body portion being bounded by a peripheral edge,
  and attachment wings extending from and hingedly attached to the backing sheet along a fold line inside of the peripheral edge, portions of the backing sheet and of the wings being provided with adhesive areas sufficient to bind the article to an undergarment to hold the article in place,
  substantially all of the adhesive areas on the wings being offset from the adhesive areas on the backing sheet so that if the wings are properly folded about the fold lines towards the adhesive areas on the backing sheet without an undergarment in place and with any release paper removed, the adhesive areas on the wings cannot contact the adhesive areas on the backing sheet.

In accord with another aspect of the invention, there is provided a method of preventing premature contact of an adhesive area on a wing of a disposable feminine hygiene article, and an adhesive area on a backing sheet of the article, the article further including a main body portion bounded by a peripheral edge, the wing being hingedly attached to the backing sheet along a fold line located inside the peripheral edge and biased to fold along the fold line towards and in contact with the backing sheet; the method comprising the steps:
  a) placing the adhesive on the backing sheet in predetermined areas on the sheet, and
  b) placing substantially all of the adhesive area on the wing at places that are offset from the predetermined adhesive areas on the backing sheet, so that contact between the wing and the backing sheet due to the bias in the absence of an undergarment, will not place adhesive in contact with adhesive.

In accord with yet another aspect of the invention, there is provided a method of attaching a disposable feminine hygiene article to an undergarment, comprising the steps of:
  a) providing the article with a main body of absorbent material mounted on an impervious backing sheet, and opposing wings foldably projecting from the backing sheet to assist in attachment to an undergarment, the backing sheet and the wings each having pressure-sensitive adhesive areas optionally covered with removable release paper, the adhesive areas of the backing sheet occupying at least 50% of the total surface area of the backing sheet, the wings being each foldable towards the backing sheet along a fold line;
  b) removing any release paper from all of the adhesive areas;
  c) attaching the adhesive area of the backing sheet to one side of a suitable undergarment; and
  d) attaching the adhesive areas of the wings to a side of the undergarment opposite to the one side by folding over the wings about the fold lines so that, with the undergarment in-between, substantially all adhesive areas of the wings are offset from the adhesive areas of the backing sheet;
    whereby any inadvertent folding over of the wings in the absence of an undergarment will not adhere a wing to the adhesive areas of the backing sheet because the adhesive areas of wings and backing sheet are not superimposed.

As used herein, "substantially all adhesive areas are offset" means, a deliberate positioning such that the offset condition occurs for all the adhesive areas during normal manufacture and application of the article. It does not mean to exclude the case wherein a negligible amount of the adhesive areas happen to overlap due to either accidental variations during manufacture, or mis-applications during use of the article. As used herein, "negligible" means, a misplacement of the adhesive and thus an overlap that does not exceed about 5 mm lineal distance.

Also as used herein, a "fold line" can be curved or straight, and when referring to the fold line of the wing, it means the line along which the wing is first free to fold relative to the main body. Additionally there may be other portions of the wing more distal from the fold line and the main body, that also are foldable.

Accordingly, it is an advantageous feature of the invention that a disposable feminine hygiene article with back-attached wings is provided that adheres to an undergarment by the use of adhesive areas, so constructed that the adhesive areas of the wings cannot inadvertently and ruinously stick, when exposed for use, to the other adhesive areas in the absence of an undergarment between them.

Other advantageous features will become apparent upon reference to the following Detailed Description, when read in light of the attached drawings.

DESCRIPTION OF THE PREFERRED EMBODIMENTS

The invention is described hereinafter in connection with certain preferred embodiments, in which the wings are back-attached by a particular method of folding wings that are initially contiguous extensions of the backing sheet, about the peripheral edge of the main body portion to adhesively secure the wings to a portion of the backing sheet, creating a fold line that is interior of the peripheral edge, and a bias to force the wing towards the backing sheet. Also, certain adhesive patterns are described that are preferred to achieve the adhesive offsets. In addition, the invention is applicable regardless of how the wings achieve their back-attached configuration, and regardless of the actual patterns of adhesive areas, so long as those of the wings are offset from those of the backing sheet when the wings are folded towards the backing sheet.

Figure 1:
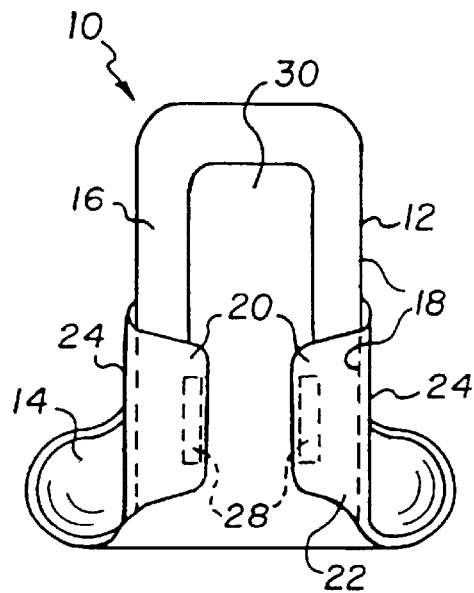
FIG. 1 is an isometric view of a disposable feminine hygiene article of the prior art, such as is described in the aforesaid WO 94/13237 application.

FIG. 1 illustrates a problem of the prior art construction. Feminine hygiene article 10 comprises a main body portion 12 comprising a pad 14 of absorbent material and an impervious backing sheet 16 on which pad 14 is mounted. Body portion 12 has peripheral edges 18 that define the boundary of the portion 12. In addition, attachment wings 20,22 are formed as contiguous extensions of sheet 16, and fold about a fold line 24 back toward the backing sheet 16. An adhesive area 28 is provided on each wing, facing towards sheet 16, and a much larger area 30 of adhesive is formed on backing sheet 16, facing the wings.

In use, wings 20,22 are folded as shown, with an undergarment interposed between body portion 12 and the wings, to attach article 10 to the garment. However, if this should happen prematurely, that is, without the garment in place, then adhesive area 20 or 22, or both, can contact adhesive area 30, and because of their tackiness at room temperature, irretrievably stick to each other. (As used herein, "room temperature" means, any temperature at which a user can be expected to apply the article to an undergarment, including from 0° C. up to about 38° C.) Although this problem is shown in the context of an article wherein the wings are not back-attached, but rather, are contiguous wings, a similar problem occurs with certain back-attached wings of the prior art.

Figure 3:
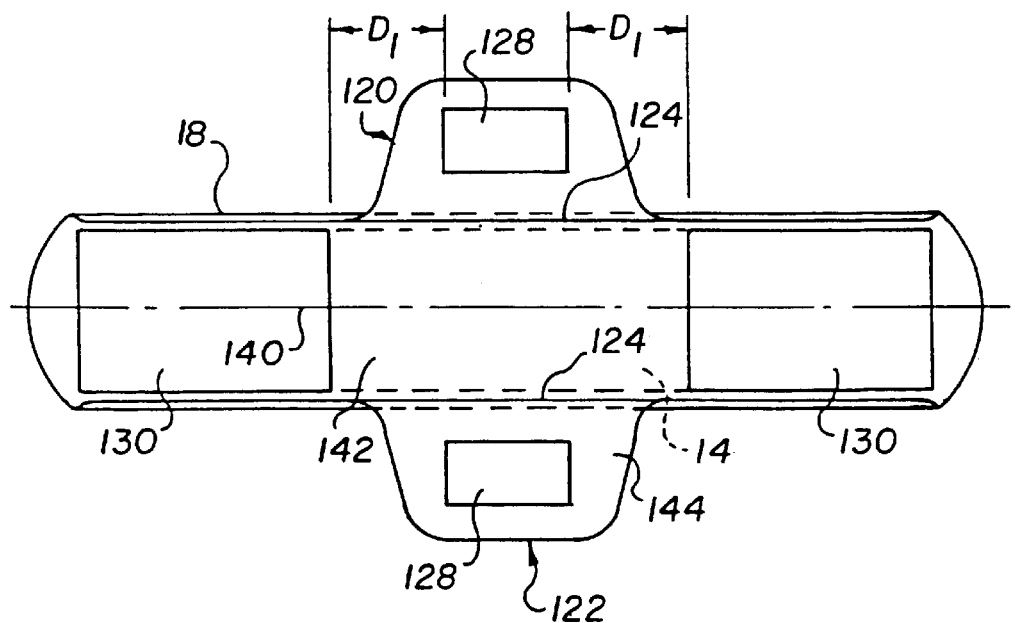
FIG. 3 is a plan view similar to that of FIG. 2, but with the wings unfolded as they might be prior to attachment to an undergarment, further illustrating the offset effect of the adhesive areas.
Figure 2:
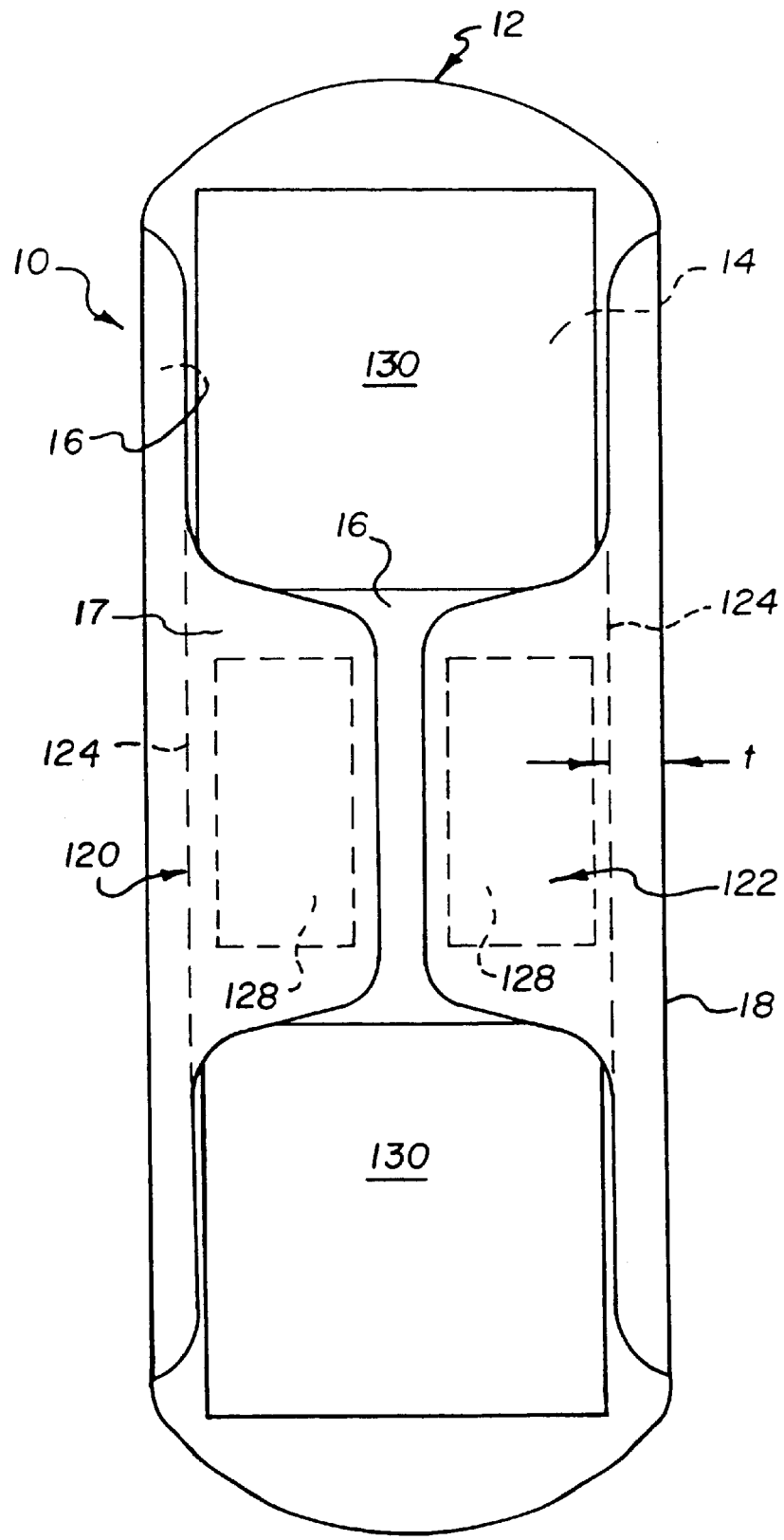
FIG. 2 is a plan view of a disposable feminine hygiene article prepared in accordance with the invention.

In contrast, an article 10 manufactured in accord with the invention, FIGS. 2–3, comprises a main body portion 12 having an absorbent material pad 14 (shown in phantom, FIG. 3) attached in a conventional manner to backing sheet 16, preferably by being sandwiched between the backing sheet 16 and a conventional porous cover sheet 17. The cover sheet and the backing sheet are laminated together in a conventional manner, and it is this laminate that is used to form wings 120, 122. The boundary of portion 12 is defined by peripheral edge 18. Wings 120 and 122 are back-attached wings, formed by folding contiguous portions of sheet 16 about edge 18 with adhesive located between edge 18 and an inside demarcation line 124, and securing the two portions of sheet 16 so folded together between line 124 and edge 18. This then defines a zone of attachment having a width "t" and the wings are back-attached, all as is conventional. As shown in FIG. 3, line 124 becomes the fold line for the unfolding, and folding, of the wings relative to main body portion 12, with the bias being to fold the wings up against backing sheet 16 as shown in FIG. 2.

An adhesive area 128 is provided on each wing, as well as area 130 on backing sheet 16. Areas 130 cover at least 50% of the backing sheet of portion 12 exposed to an undergarment, for better sticking.

The materials used for absorbent material 14, backing sheet 16, the adhesive areas, and release sheets, if any, are conventional and thus need no further description.

Key to the invention is that adhesive areas 128,130 are disposed to be offset from each other when the wings are folded as shown, and as biased, in FIG. 2. In this particular embodiment, as shown in FIG. 3, the offset characteristic is achieved by positioning areas 128,130 so that they are displaced from each other measured along a longitudinal axis 140 that is generally aligned with the direction of extension of body portion 12. More specifically, areas 128 which are generally centrally located along axis 140, are spaced apart a distance $D_1$ from the positioning of areas 130 on backing sheet 16, which are distally located away from the center. Stated in other words, non-adhesive areas 142, 144 are located on backing sheet 16 and wings 120,122, respectively, so as to offset the adhesive areas.

Such non-adhesive areas can be formed either by leaving those areas uncoated, as shown, or by coating all areas first with a pressure-sensitive adhesive tacky at room temperature, and over-coating that adhesive in areas 142 and 144, with a conventional non-pressure sensitive hot-melt adhesive that is non-tacky at room temperature. This leaves areas 128,130 as being coated only with the pressure-sensitive adhesive that is tacky at room-temperature.

Another alternative is to form the non-adhesive areas with a release coated surface such as a coating of a silicone release agent. For example, the release agent can be applied by coating the surface with a curable silicone emulsion that is cured in situ by UV light, or by adhering to the surface a tape that has on its exposed surface a silicone release agent.

Because adhesive areas 128,130 are offset, it is optional whether the article 10 is packaged so that adhesive areas are covered with a conventional release paper, or not.

It is not essential that the adhesive area on the backing sheet, and on the wings, be only two areas or a single contiguous area, respectively. As shown for example in FIG. 4, each area can be divided into plural areas. Parts similar to those previously described bear the same reference numeral, to which the distinguishing suffix "A" is applied.

Figure 4:
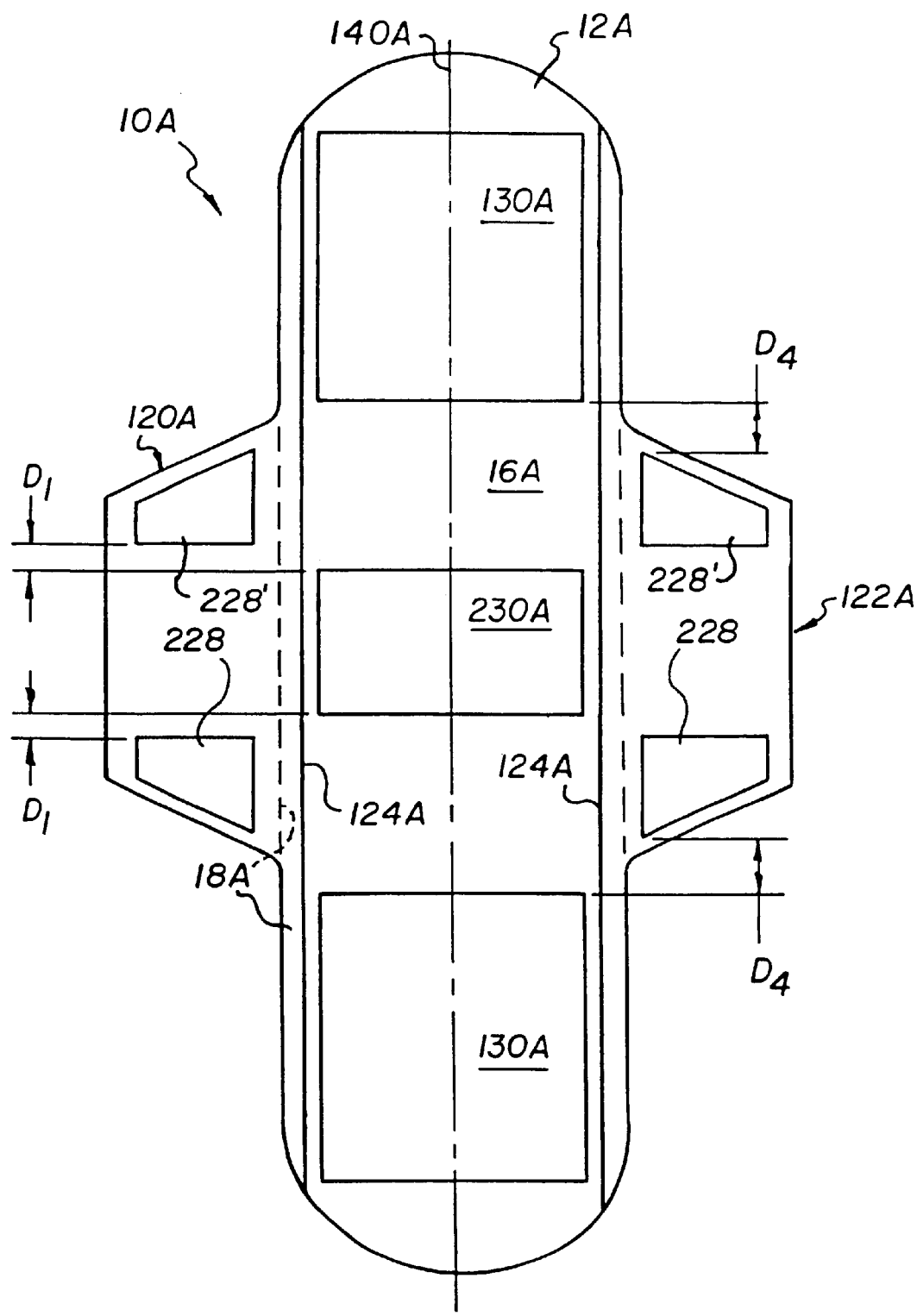
FIGS. 4 through 7 are plan views similar to that of FIG. 2, but illustrating alternate embodiments.

Thus, FIG. 4, article 10A comprises a main body portion 12A circumscribed by peripheral edge 18A, wings 120A and 120A being back-attached by adhering backing sheet 16A to itself inside of edge 18A to create fold line 124A, as in the previous embodiment. However, unlike the previous embodiment, the adhesive area on each wing comprises two spaced apart areas 228,228', and the adhesive area on backing sheet 16A inside peripheral edge 18A is split into three spaced apart areas 130A, 130A, and 230. At least 50% of the area of sheet 16A on main body portion 12A is covered with adhesive areas 130A, 130A and 230. As before, the adhesive areas on the wings are offset from the adhesive areas on the backing sheet of the main body portion, by displacing the wing areas 228,228' along longitudinal axis 140A from the positions along that axis where the main body portion areas 130A, 130A, and 230 are located. More specifically, wing areas 228,228' are displaced along axis 140A a distance $D_1$ from main body portion area 230 and a distance $D_4$ from the other two main body portion areas 130A,130A.

Although distance $D_4$ is shown as being larger than distance $D_1$, this is not essential and can be, reversed. Indeed, there is no reason why the two distances $D_1,D_1$ on wing 120A need to equal each other or the corresponding distances $D_1,D_1$ on wing 122A, other than for ease in manufacture. Likewise, distances $D_4,D_4$ for each wing 120A,122A need not equal each other or the distances $D_4,D_4$ on the other wing.

One advantage of FIG. 4's embodiment, which makes it a highly preferred embodiment, is that the additional adhesive area 230 on the main body portion helps the article adhere better to an undergarment, than is the case if area 230 is omitted.

It is not essential that the offsetting of the wing adhesive areas from those on the main body portion, be achieved by displacement longitudinally along the longitudinal axis. Instead, FIG. 5, the displacement can be measured transversely from the axis. Parts similar to those previously described bear the same reference numeral, to which the distinguishing suffix "B" is applied. Thus, article 10B comprises a main body portion 12B circumscribed by peripheral edge 18B, and two back-attached wings 120B and 122B that fold away from body portion 12B and longitudinal axis 140B, along fold line 124B, all in the manner described for the two previous embodiments. Each wing has a single adhesive area 128B. Main body portion 12B has on its backing sheet 16B a plurality of adhesive areas 130B,130B similar to that of FIG. 3, and in addition, two additional areas 330,330' disposed between areas 130B,130B. The total adhesive area of 130B, 130B, and 330, 330' is more than 50% of the area of sheet 16B of body portion 12B.

Unlike the previous embodiments, the offsetting of the wing adhesive areas is achieved by locating them a predetermined minimum distance $D_2$ from fold line 124B that is different from, e.g., greater than, the maximum distance $D_3$ that adhesive areas 330,330' are located from the same fold line. In this manner, when the wings are properly folded inwardly, areas 128B will fall in the area shown in phantom, between adhesive areas 330,330'. (It will be appreciated that area 128B must not extend so far out on the wing 120B as to overlap, when folded back, adhesive area 330', and likewise for adhesive area 128B on wing 122B, relative to adhesive area 330. That is, maximum distance $D_5$<minimum distance $D_6$.)

To discourage a user from folding the wings back towards body portion 12B along fold lines other than fold line 124B, and thus potentially to overlap adhesive area 128B with one of areas 330 or 330', conventional stiffeners 340 are optionally formed in wing 122B (shown) and wing 120B (not shown), between fold line 124B and adhesive 128B. For example, stiffeners 340 can be embossed into the fabric of the wing.

Figure 6:
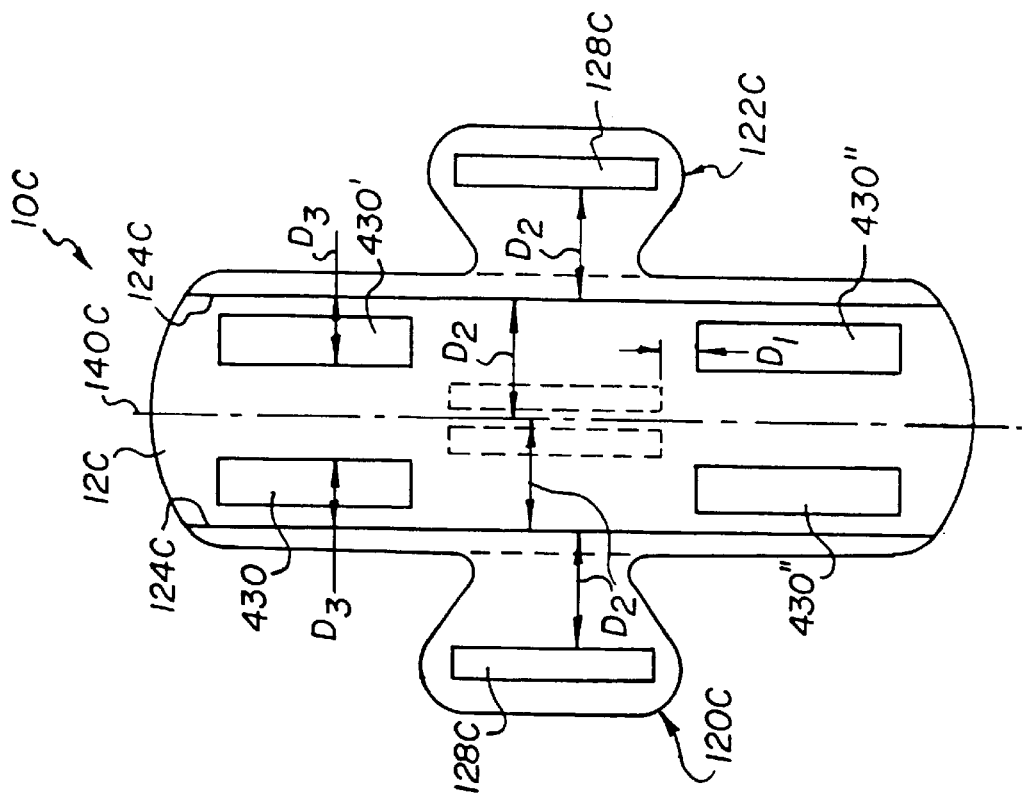
Figure 5:
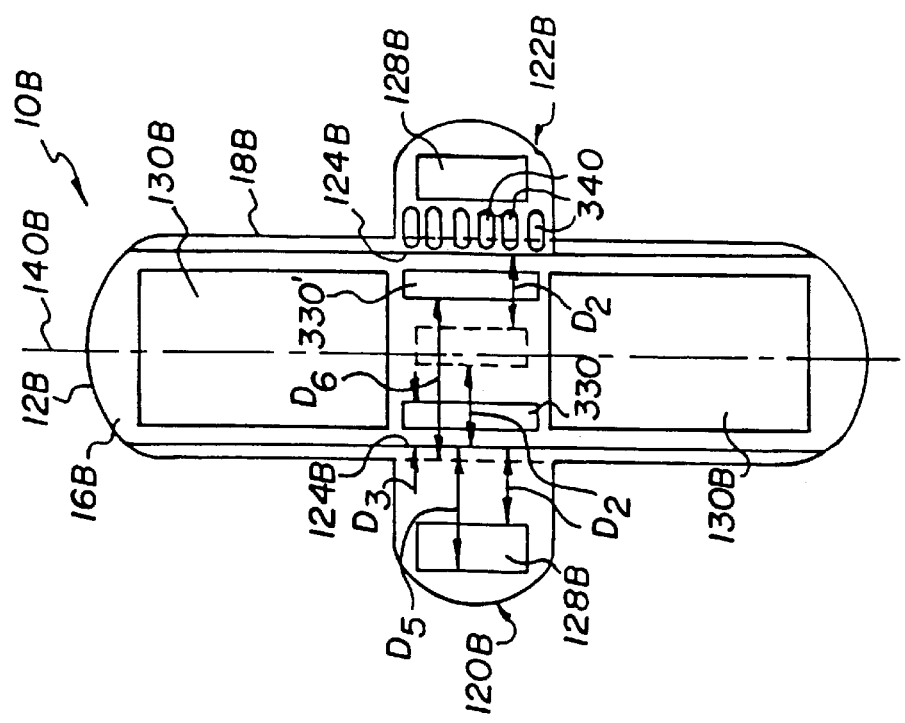

As a further embodiment of the invention, it is of course, feasible, FIG. 6, to combine the features of both FIGS. 4 and 5, so that the wing adhesive areas are offset from the adhesive areas on the main body portion measured both along the longitudinal axis, and as measured transversely from the wing fold lines. Parts similar to those previously described bear the same reference numeral, to which the distinguishing suffix C is appended.

Thus, article 10C comprises main body portion 12C and back-attached wings 120C and 122C that fold along fold lines 124C. Adhesive areas 128C are placed on the wings, and adhesive areas are also placed on the main body portion. However, the latter comprise four spaced apart areas 430, 430', 430", and 430'". These four are displaced longitudinally along longitudinal axis 140C by a distance $D_1$ from the location along that axis of wing areas 128C. Furthermore, they are located a maximum distance $D_3$ from fold line 124C, which is less than the minimum distance $D_2$ for the location of wing areas 128C. Hence, when wing areas 128C are folded towards body portion 12C, they locate in the areas shown in phantom that are offset both along the longitudinal axis, and as measured transversely from the fold lines, compared to areas 430, 430', 430", and 430'".

Figure 7:
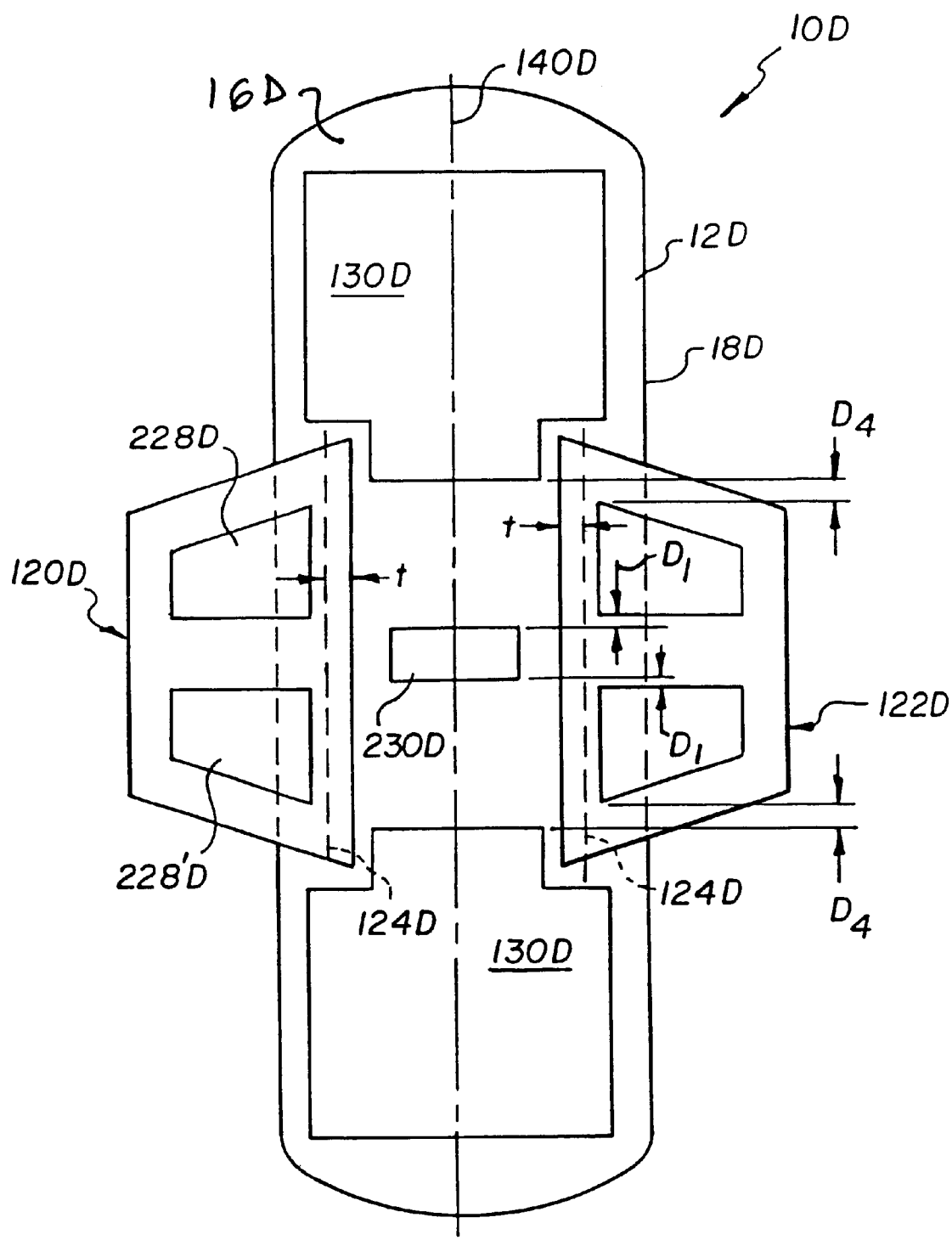

FIG. 7 illustrates the invention when applied to a back-attached wing that is a piece of fabric separate from the main body, but which is attached such as by adhesive, or by a heat-seal, in a manner similar to U.S. Pat. No. 4,900,320. Similar parts have the same reference numeral but for the appendix D.

Thus, article 10D has main body portion 12D with back-attached wings 120D,122D separately formed and adhered along thickness "t", to the backing sheet 16D of body potion 12D, producing a fold line 124D inside peripheral edge 18D. Wing adhesive areas 228D and 228'D on each wing are offset from areas 130D and 230D by being displaced longitudinally along the axis 140D distances $D_1$ and $D_4$, similar to the embodiment of FIG. 4. Thus, unlike the case of the U.S. Pat. No. 4,900,320, the wing adhesive areas are offset from the main body adhesive areas, when the former are folded towards the latter.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. A disposable feminine hygiene article comprising: a main body portion including an absorbent material and an impervious backing sheet on which said absorbent material is mounted, said main body portion being bounded by a peripheral edge and two wings, each wing extending from and hingedly attached to said backing sheet along a fold line inside of said peripheral edge respectively, portions of said backing sheet and of said wings being provided with adhesive areas sufficient to bind said article to an undergarment to hold said article in place, said portions of said backing sheet comprising one or more sections of the backing sheet located intermediate said wings, substantially all of said adhesive areas on said wings being offset from said adhesive areas on said backing sheet so that if said wings are folded about said fold lines towards said adhesive areas on said backing sheet without an undergarment in place and with any release paper removed, said adhesive areas on said wings cannot contact said adhesive areas on said backing sheet, wherein said adhesive areas on said wings is offset from said adhesive areas on said backing sheet by an area that is non-tacky at room temperature and wherein said areas that are non-tacky at room temperature comprise a first layer of pressure-sensitive adhesive, and on top of said first layer, a layer of non-pressure sensitive hot melt adhesive that is non-tacky at room temperature.

2. An article as defined in claim 1, wherein said wings comprise a contiguous extension of said backing sheet, a portion of said wings being folded about and adhesively secured to a portion of said backing sheet so as to permanently overlap a portion of said backing sheet between said fold lines and said portion of said peripheral edge, said wings being biased to fold along said fold lines towards and in contact with said backing sheet, so that the offset of said adhesive areas prevents adhesive-to-adhesive contact between wing and backing sheet.

3. An article as defined in claim 1, wherein said body portion has a longitudinal axis, and wherein said adhesive areas on said wings are offset from said adhesive areas on said backing sheet by being located at positions on said wings displaced along said longitudinal axis from the positions where said backing adhesive areas are located.

4. An article as defined in claim 1, wherein said body portion has a longitudinal axis, and wherein said adhesive areas on said wings are offset from said adhesive areas on said backing sheet by being located at predetermined distances from said fold lines that are different from the predetermined distances from said fold lines at which said backing adhesive areas are located.

5. An article as defined in claim 1, wherein at least 50% of the area of said backing sheet of said body portion is occupied by said adhesive areas.

6. An article as defined in claim 1, wherein said wings each further include stiffeners positioned to stiffen and keep each wing generally flat, so that a wing resists buckling and folding on itself such as can cause adhesive areas on the wing to misalign with the portions of the backing sheet not bearing any adhesive areas.

7. An article as defined in claim 1, wherein said adhesive areas are free of release paper.

* * * * *